(12) United States Patent
Thorson et al.

(10) Patent No.: US 12,396,871 B2
(45) Date of Patent: Aug. 26, 2025

(54) DEVICES AND METHODS FOR STENT GRAFT EXTRACTION

(71) Applicants: Brian Thorson, Mequon, WI (US); Kellie R. Brown, Waterford, WI (US); Benjamin Heard, Waukesha, WI (US)

(72) Inventors: Brian Thorson, Mequon, WI (US); Kellie R. Brown, Waterford, WI (US); Benjamin Heard, Waukesha, WI (US)

(73) Assignee: HJARTA CARE, LLC, Waukesha, WI (US)

( * ) Notice: Subject to any disclaimer, the term of this patent is extended or adjusted under 35 U.S.C. 154(b) by 117 days.

(21) Appl. No.: 17/833,487

(22) Filed: Jun. 6, 2022

(65) Prior Publication Data
US 2022/0296401 A1 Sep. 22, 2022

Related U.S. Application Data

(63) Continuation of application No. 17/088,102, filed on Nov. 3, 2020, now Pat. No. 11,351,047.

(51) Int. Cl.
| A61F 2/962 | (2013.01) |
| A61F 2/07 | (2013.01) |
| A61F 2/95 | (2013.01) |
| A61L 29/02 | (2006.01) |
| A61L 29/14 | (2006.01) |
| A61M 25/00 | (2006.01) |

(52) U.S. Cl.
CPC .............. *A61F 2/962* (2013.01); *A61F 2/07* (2013.01); *A61L 29/02* (2013.01); *A61L 29/14* (2013.01); *A61F 2002/9528* (2013.01); *A61F 2230/0069* (2013.01); *A61M 25/0009* (2013.01)

(58) Field of Classification Search
CPC .... A61F 2/962; A61F 2/95; A61F 2/07; A61F 2/82; A61F 2/2427; A61F 2/2436; A61F 2/011; A61F 2002/9528; A61F 2002/0072; A61F 2230/0069; A61F 2/95522; A61F 2/9525; A61M 25/0009; A61L 29/02; A61L 29/14
See application file for complete search history.

(56) References Cited

U.S. PATENT DOCUMENTS

| 4,594,996 | A | | 6/1986 | Ibrahim et al. | |
| 5,725,519 | A | * | 3/1998 | Penner | A61F 2/9525 606/1 |
| 5,785,715 | A | * | 7/1998 | Schatz | A61B 17/22032 606/1 |

(Continued)

OTHER PUBLICATIONS

International Search Report and Written Opinion corresponding to PCT PCT/US2021/057941 dated Jan. 31, 2022, 7 pages.

*Primary Examiner* — Robert A Lynch
(74) *Attorney, Agent, or Firm* — FOLEY & LARDNER LLP

(57) ABSTRACT

A device for extracting an endovascular stent graft from a vessel including a cylindrical body and an opening formed in the cylindrical body. The cylindrical body has a first open end, a second open end, and a sidewall surrounding a hollow bore of the cylindrical body. The opening is formed in the sidewall between the first open end and the second open end forming a first ring portion at the first open end and a second ring portion at the second open end. Additionally, a diameter of the first open end is greater than a diameter of the second open end.

19 Claims, 5 Drawing Sheets

(56) References Cited

U.S. PATENT DOCUMENTS

| | | | | |
|---|---|---|---|---|
| 6,022,333 | A | * | 2/2000 | Kensey ................ A61M 1/28 604/29 |
| 6,027,508 | A | | 2/2000 | Ren et al. |
| 11,351,047 | B2 | * | 6/2022 | Thorson ................ B33Y 80/00 |
| 2002/0111649 | A1 | * | 8/2002 | Russo ............... A61M 25/0074 606/200 |
| 2004/0097904 | A1 | * | 5/2004 | Carrillo ............ A61M 25/0029 604/528 |
| 2006/0142703 | A1 | * | 6/2006 | Carter ............... A61M 25/0043 264/138 |
| 2007/0067013 | A1 | * | 3/2007 | Karpiel ................ A61F 2/966 623/1.12 |
| 2007/0112306 | A1 | * | 5/2007 | Agnew ............. A61M 25/0021 604/164.13 |
| 2014/0155930 | A1 | * | 6/2014 | Bennett ................ A61F 2/011 606/200 |
| 2014/0171958 | A1 | | 6/2014 | Baig |
| 2016/0278955 | A1 | * | 9/2016 | Liu .......................... B65B 5/04 |
| 2018/0360629 | A1 | | 12/2018 | Bernard et al. |

* cited by examiner

DEVICES AND METHODS FOR STENT GRAFT EXTRACTION

CROSS-REFERENCE TO RELATED APPLICATIONS

This application is a continuation of U.S. patent application Ser. No. 17/088,102, filed Nov. 3, 2020, which is hereby incorporated by reference herein in its entirety.

BACKGROUND

The present invention relates generally to the field of endovascular stent graft extraction, and more particularly to devices and methods for atraumatic stent grant extraction.

An endovascular stent graft may be used for a variety of conditions involving the blood vessels, but most commonly to reinforce a weak spot in an artery called an aneurysm. Over time, blood pressure and other factors can cause this weak area to bulge and eventually enlarge and rupture. A stent graft is implanted to tightly seal with the artery above and below the aneurysm. The graft is stronger than the weakened artery and allows blood to pass through it without pushing on the bulge.

Occasionally, extraction of the stent graft is necessary due to infection or failure of the original implant to perform as intended. Because the stent graft typically includes prongs which engage with the vessel wall, extraction of the device can cause significant damage to the tissue to which it is engaged. Stent graft explant is known to be associated with high morbidity, caused by a confluence of factors. Damage caused to the vessel wall during the extraction process is one factor that contributes to the high morbidity.

Accordingly, there is a need for a device that promotes atraumatic removal of a stent graft from a vessel.

SUMMARY OF THE INVENTION

At least one embodiment relates to a device for extracting an endovascular stent graft from a vessel. The device includes a cylindrical body and an opening formed in the cylindrical body. The cylindrical body has a first open end, a second open end, and a sidewall surrounding a hollow bore of the cylindrical body. The opening is formed in the sidewall between the first open end and the second open end forming a first ring portion at the first open end and a second ring portion at the second open end. Additionally, a thickness of the sidewall at the first open end tapers toward the opening and wherein a thickness of the sidewall at the second open end tapers toward the opening such that the hollow bore is narrower at each end than at the opening.

Another embodiment relates to a method for extracting an endovascular stent graft from a vessel. The method includes the steps of inserting an extraction device into the vessel. The extraction device including a cylindrical body and an opening formed in the cylindrical body. The cylindrical body has a first open end, a second open end, and a sidewall surrounding a hollow bore of the cylindrical body. The opening is formed in the sidewall between the first open end and the second open end forming a first ring portion at the first open end and a second ring portion at the second open end. Additionally, a thickness of the sidewall at the first open end tapers toward the opening and wherein a thickness of the sidewall at the second open end tapers toward the opening such that the hollow bore is narrower at each end than at the opening. The method further includes sliding the extraction device over the stent graft such that the first open end slides between a vessel wall and the stent graft to compress the stent graft within the first ring portion, continue sliding the extraction device over the stent graft until the extraction device causes a prong of the stent graft to release from the vessel wall, and removing at least one of the stent graft and the extraction device from the vessel while the sidewall is located at least partially between the stent graft and the vessel wall.

This summary is illustrative only and should not be regarded as limiting.

BRIEF DESCRIPTION OF THE DRAWINGS

A clear conception of the advantages and features constituting the present disclosure, and of the construction and operation of typical mechanisms provided with the present disclosure, will become more readily apparent by referring to the exemplary, and therefore non-limiting, embodiments illustrated in the drawings accompanying and forming a part of this specification, wherein like reference numerals designate the same elements in the several views, and in which.

Figure 1A:
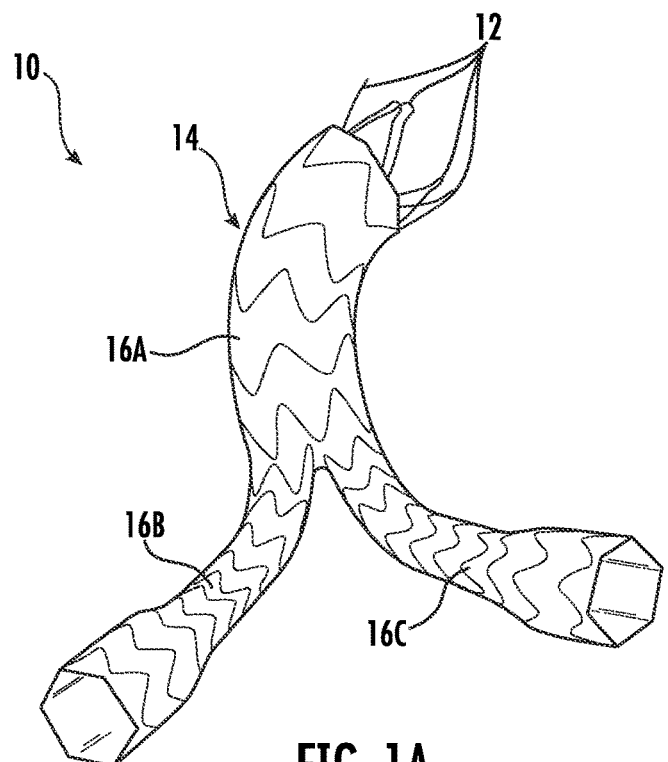
FIG. 1A is a perspective view of an endovascular stent graft for use in an abdominal aorta, according to an exemplary embodiment.

The foregoing and other features of the present disclosure will become apparent from the following description and appended claims, taken in conjunction with the accompanying drawings. Understanding that these drawings depict only several embodiments in accordance with the disclosure and are therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Referring generally to the figures, described herein is an endovascular stent graft extraction device. The endovascular stent graft extraction device includes a cylindrical body extending from a first open end to a second open end and a sidewall surrounding a hollow bore of the cylindrical body. The first open end defines a first aperture, and the second open end defines a second aperture. The sidewall further includes an opening that is located between the first open end and the second open end and concurrent with a curve in the cylindrical body. The sidewall further includes a taper (e.g., an increase in inner diameter of the cylindrical body) from proximate the first aperture of the first open end to the opening and from the second aperture of the second open end to the opening. Additionally, the sidewall further includes a blunt or rounded edge at the first opening and the second opening.

In use, the endovascular stent graft extraction device is inserted into a vessel (e.g., one or more portions of the aorta, one or more arteries, etc.) such that the first open end or the second open end is first received within the vessel. Once inserted, the endovascular stent graft extraction device is slid over and around the stent graft such that the first open end slides between a vessel wall and the stent graft to compress the stent graft within the first ring portion. Then, the endovascular stent graft extraction device continues to be slid over the stent graft until the device causes a prong of the stent graph to release from a wall of the vessel. Lastly, the endovascular stent graft extraction device and the stent graft are removed from the vessel such that the sidewall of the endovascular stent graft extraction device is at least partially between the stent graft and the vessel during removal.

Figure 1B:
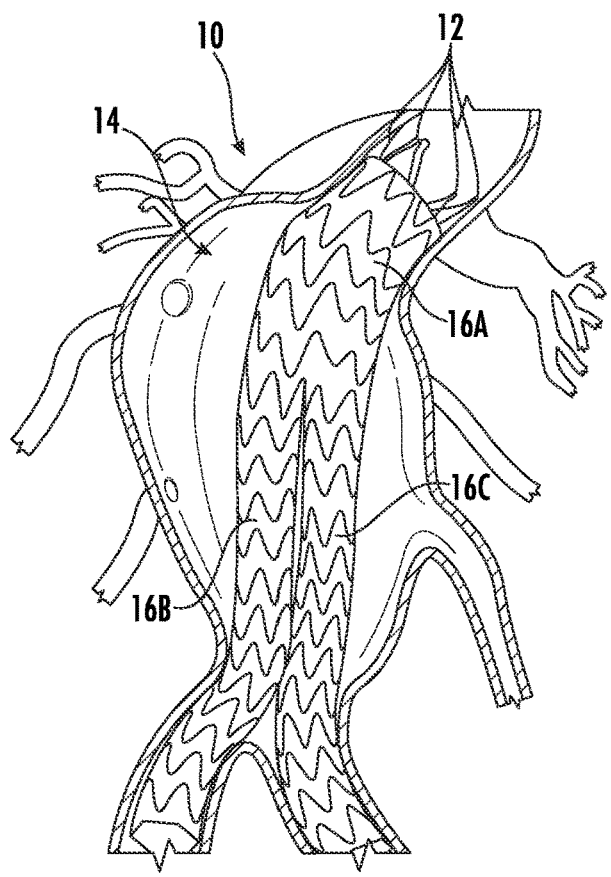
FIG. 1B is a partial view of the endovascular stent graft of FIG. 1 implanted into the abdominal aorta.

Referring to FIGS. 1A-1B, an endovascular stent graft 10 is shown. The endovascular stent graft 10 is configured to be implanted within one or more various arteries of a person, for example a patient with an aneurysm, to reinforce the walls of the artery. In some embodiments, the endovascular stent graft 10 is specifically configured to be used in the abdominal aorta and the iliac arteries branching off of the abdominal aorta (FIG. 1B). To do so, the endovascular stent graft 10 includes multiple prongs 12 and a frame 14 having an aortic portion 16A and one or more artery portions (e.g., branches) 16B and 16C. Each portion may further include a respective central axis (not shown) along which the frame extends. The frame 14 can be made of a variety of materials configured to be implanted within arteries and provides the support to reinforce the walls of the arteries from bursting. Additionally, to secure the endovascular stent graft 10, the frame 14 may be configured to collapse and expand along a respective central axis (e.g., the length of the frame 14 can change) but to be biased in such a way that it acts rigid or solid radial to the central axis (e.g., the diameter of the portions of the frame 14 does not change). In this way, the frame 14 supports the walls of the arteries (e.g., the abdominal aorta and the iliac arteries branching off of the abdominal aorta) but is able to be expanded and contracted for implantation. Similarly, the frame 14 includes the aortic portion 16A (a relatively wide portion) and the one or more artery portions 16B and 16C (relatively narrower portions). In other embodiments, the frame 14 may include other portions (e.g., more branches, fewer branches, no aortic portion, etc.) depending on where the endovascular stent graft 10 is to be used.

The prongs 12 are coupled to the aortic portion 16A and are configured to selectively move between a deployed position in which they press against the walls of the artery and prevent movement of the endovascular stent graft 10 and a non-deployed position in which they do not press against the walls of the artery and do not prevent movement of the endovascular stent graft 10. In some embodiments, the prongs are coupled to other portions of the frame 14. In the deployed position (FIGS. 1A and 1B), the prongs 12 extend at least partially radially outward from the central axis of the aortic portion 16A and press against the walls of the aorta (or artery) to prevent the endovascular stent graft 10 from moving. By doing so, the prongs 12 may dig in or provide a friction force that keeps the endovascular stent graft 10 in place. To do so and while being implanted, a special device may be required to move the prongs 12 into the deployed position. In the non-deployed position (not shown), the prongs 12 do not extend radially outward or contact the walls of the aorta. By doing so, the endovascular stent graft 10 is able to be moved around within the arteries to be correctly positioned to cover the aneurysm. Once in place, the prongs 12 may be selectively moved to the deployed position and "implanted" within the aorta. At this point, the endovascular stent graft 10 can be left in the aorta for long periods of time (e.g., permanently, multiple years, etc.) without moving to prevent the walls of the aorta (or arteries) from rupture.

Figure 2:
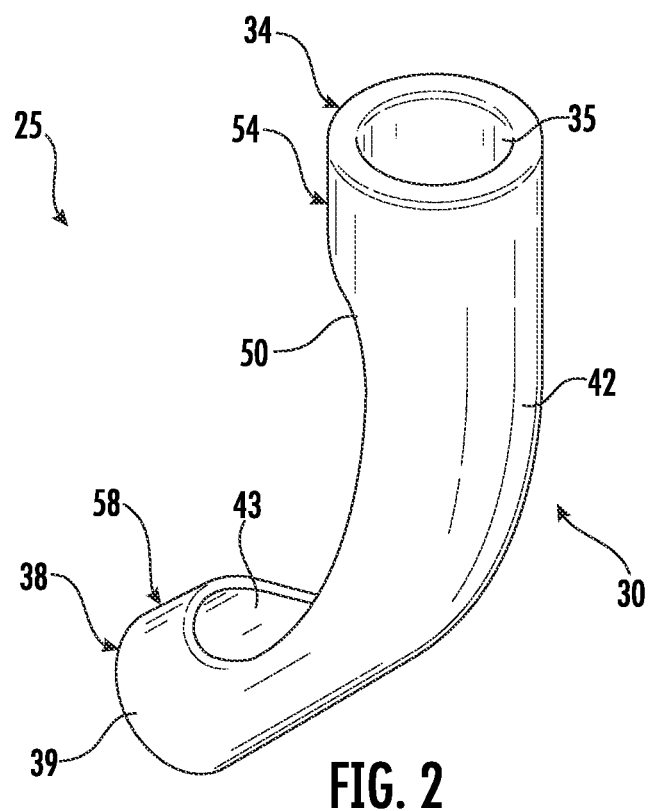
FIG. 2 is a perspective view of an endovascular stent graft extraction device, according to an exemplary embodiment.
Figure 3:
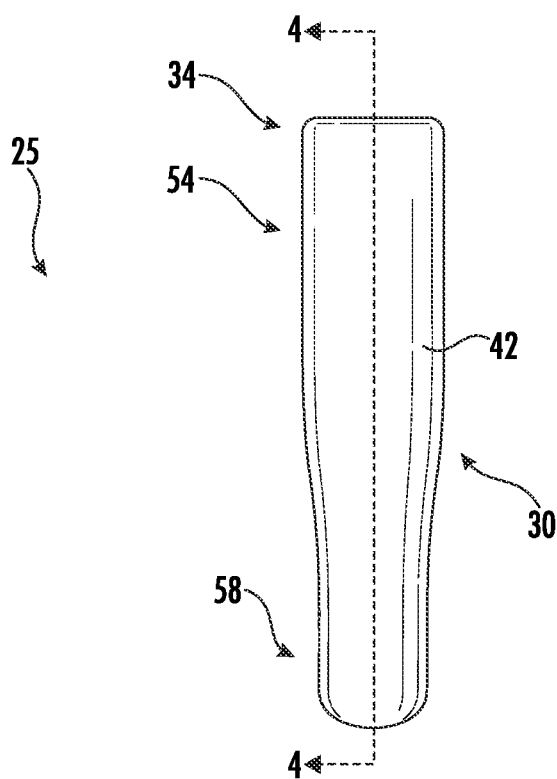
FIG. 3 is a rear view of the endovascular stent graft extraction device of FIG. 2.
Figure 4:
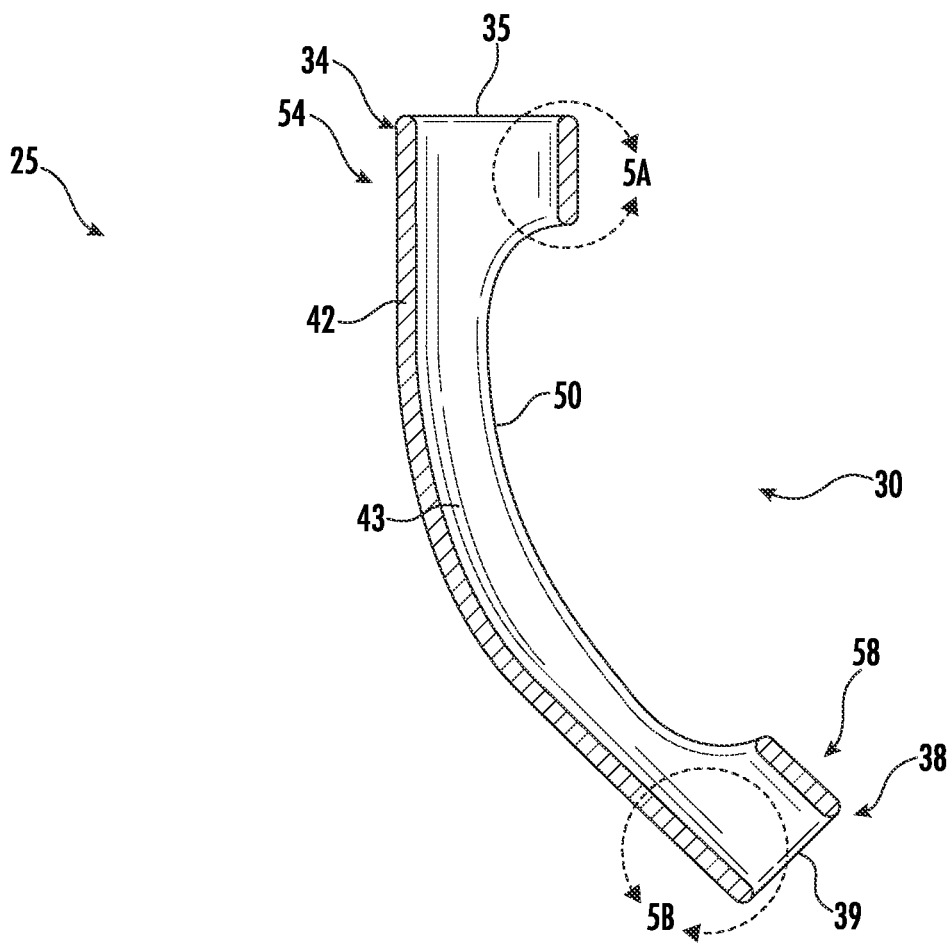
FIG. 4 is a section view of the endovascular stent graft extraction device of FIG. 3 along line 4-4.

Referring now to FIGS. 2-4, an endovascular stent graft extraction device 25 is shown, according to an exemplary embodiment. While the endovascular stent graft 10 is configured to be left in the aorta (or arteries) for long periods of time, various complications may develop (e.g., infection, the endovascular stent graft 10 not deploying correctly, swelling of the arteries, plaque buildup, failure, etc.) which require the removal of the endovascular stent graft 10. The endovascular stent graft extraction device 25 is therefore configured to be inserted within the arteries and to be used to extract the endovascular stent graft 10 atraumatically (e.g., with little to no damage to the arteries themselves). To do so, the endovascular stent graft extraction device 25 includes a cylindrical body 30 including a first open end 34 having a first aperture 35, a second open end 38 having a second aperture 39, and a sidewall 42 extending between the first open end 34 and the second open end 38 such that it defines a hollow bore 43 of the cylindrical body 30. The cylindrical body 30 may be of various rigid materials that are suitable for sterilization such as surgical/medical grade steel, stainless steel, and surgical/medical grade plastic. In some embodiments, the cylindrical body 30 may be manufactured using 3D printing methods (e.g., Stereolithography (SLA), Selective Laser Sintering (SLS), Fused Deposition Modeling (FDM), Direct Metal Laser Sintering (DMLS), or other conventional 3D printing methods). Beneficially and by doing so, one or more dimensions of the endovascular stent graft extraction device 25 (e.g., diameter of the sidewall 42, length of the sidewall 42, etc.) may be easily changed or updated based on the specific aorta or arteries within which the device is working, or based on the specific endovascular stent graft 10 that is being extracted. While the aorta and arteries are typically a common diameter and length for a certain age and size of a patient, they may vary depending on genetics, prior surgeries, and other environmental factors. As a result, the endovascular stent graft extraction device 25 may be manufactured using 3D printing methods so the various dimensions may be easily and quickly updated, such as right on site at a surgical center or hospital.

In use (e.g., to extract the endovascular stent graft 10), the endovascular stent graft extraction device 25 is inserted into the aorta or the artery such that the first open end 34 or the second open end 38 (or both) are located within the walls of the aorta or artery. The first aperture 35 and the second aperture 39 may include outer diameters that are sized with respect to the aorta or artery such that they are at least partially smaller than the diameter of the walls of the aorta or artery. For example, the apertures 35, 39 may have a diameter between approximately 15-30 millimeters (mm). In some embodiments, the first aperture 35 and the second aperture 39 have different outer diameters. For example, the first aperture 35 may have an outer diameter between approximately 24-26 mm and the second aperture 39 may have an outer diameter between approximately 18-20 mm. Once inserted into the aorta or artery, the endovascular stent graft extraction device 25 may be slid (e.g., pushed, moved, etc.) along the wall of the aorta until it comes to the frame 14 of the endovascular stent graft 10. At this point, as will be discussed further herein, the sidewall 42 may come between the wall of the aorta and the frame 14 such that the frame 14 is located within the hollow bore 43. Once the sidewall 42 proximate the first aperture 35 or the second aperture 39 reaches the prongs 12, the endovascular stent graft extraction device 25 may be configured to move the prongs 12 from the deployed position to the non-deployed position. At this point, the user of the endovascular stent graft extraction device 25 may extract the endovascular stent graft 10.

In regards to further dimensions, the cylindrical body 30 may include a height (along vertical axis in FIG. 4) from the first aperture 35 to the second aperture 39 of approximately 90-120 mm or approximately 107 mm. In other embodiments, the cylindrical body 30 includes a length (e.g., along the center of the arc/center of the sidewall 42) from the aperture 34 to the second aperture 39 of approximately 100-150 mm or approximately 120 mm. As described herein, the first aperture 35 may have an outer diameter approximately 24-26 millimeters (mm) or approximately 25 mm, and an inner diameter approximately 14-20 mm or approximately 17 mm. Similarly, the second aperture 39 may have an outer diameter approximately 18-20 mm or approximately 19 mm, and an inner diameter approximately 10-14 mm or approximately 12 mm. By having a first aperture 35 with an inner diameter and an outer diameter larger than the inner diameter and the outer diameter of the second aperture 39, the endovascular stent graft extraction device 25 is better used on a variety of aorta or artery sizes. In this way, if one aperture is too large or too small, the user of the endovascular stent graft extraction device 25 can use the opposite end.

Still referring to FIGS. 2-4, the cylindrical body 30 is shown to have a circular cross section such that it includes a diameter and length and is curved along the length of the cylindrical body 30 such that it forms an arc. Additionally, the sidewall 42, between the first open end 34 and the second open end 38, defines an opening 50 along a curved section of the cylindrical body 30. In some embodiments, the opening 50 and the cylindrical body 30 are curved such that they include a radius of curvature approximately 50-90/mm or 70/mm. In other embodiments, the opening 50 is formed in the sidewall 42 at the curved portion of the cylindrical body 30 such that it is formed in a concave or a convex portion of the body. The opening 50 is a portion of the cylindrical body 30 in which the sidewall 42 defines approximately a half cylinder (e.g., the sidewall only extends around about half of the bore 43). In this way and as a result, a user of the endovascular stent graft extraction device 25 is able to access the hollow bore 43 of the cylindrical body 30 via the opening 50. Being able to access the hollow bore 43 is beneficial as it allows the user of the endovascular stent graft extraction device 25 to pull/extract the endovascular stent graft 10 (when moved to its non-deployed position) from the hollow bore 43 and through the opening 50. For example, the user may access the hollow bore 43 of the cylindrical body 30 to grab (e.g., using a clamp, a medical device, a machine, etc.) the frame 14 of the endovascular stent graft 10 (as it is located within the hollow bore 43) and then remove the endovascular stent graft 10. By doing so, the endovascular stent graft 10 does not contact the walls of the aorta or artery during removal and only contacts the sidewall 42. In this way, the opening 50 provides a location in which the user of the endovascular stent graft extraction device 25 can easily see and extract the endovascular stent graft 10.

By including the opening 50 along the curved portion of the cylindrical body 30, the sidewall 42 defines two ring portions (e.g., a first ring portion 54 and a second ring portion 58) within the cylindrical body 30. The first ring portion 54 and the second ring portion 58 are opposed with respect to the opening 50 and each includes its own respective length, center axis, inner diameter, and outer diameter. As compared to the opening 50, the ring portions 54, 58 are locations in which the sidewall 42 forms a full cylinder and not a portion (e.g., the half cylinder of the opening 50) of a cylinder. The first ring portion 54 extends from the first open end 34 to the opening 50, and the second ring portion extends from the second open end 38 to the opening 50. Additionally as the cylindrical body 30 is curved, in some embodiments, the center line of the first ring portion 54 may be offset by approximately 30-60 degrees or approximately 45 degrees from the center line of the second ring portion 58.

Figure 5A:
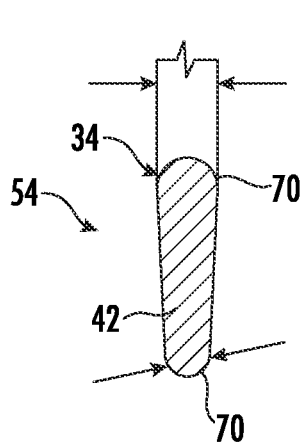
FIG. 5A is a cut-out view of a sidewall proximate a first end of the endovascular stent graft extraction device of FIG. 4.
Figure 5B:
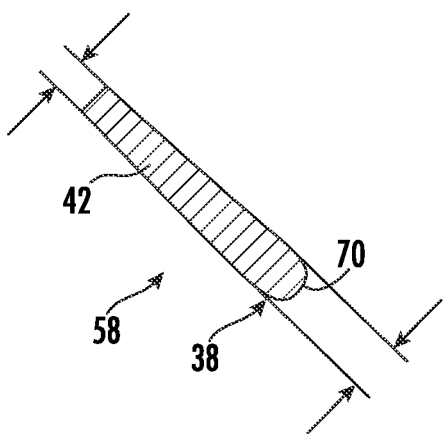
FIG. 5B is a cut-out view of the sidewall proximate a second end of the endovascular stent graft extraction device of FIG. 4.
Figure 6A:
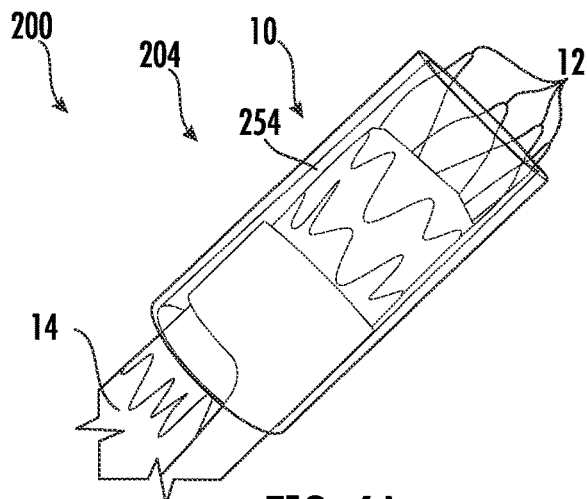
FIGS. 6A-6E is a perspective view of the endovascular stent graft extraction device of FIG. 2 being used in a method of extracting an endovascular stent graft, according to an exemplary embodiment.
Figure 6B:
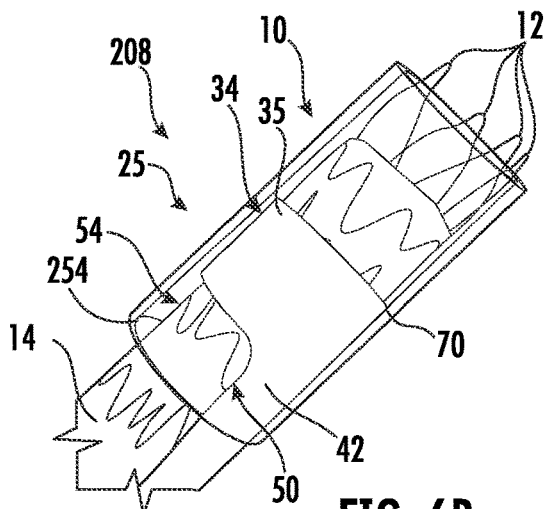
Figure 6C:
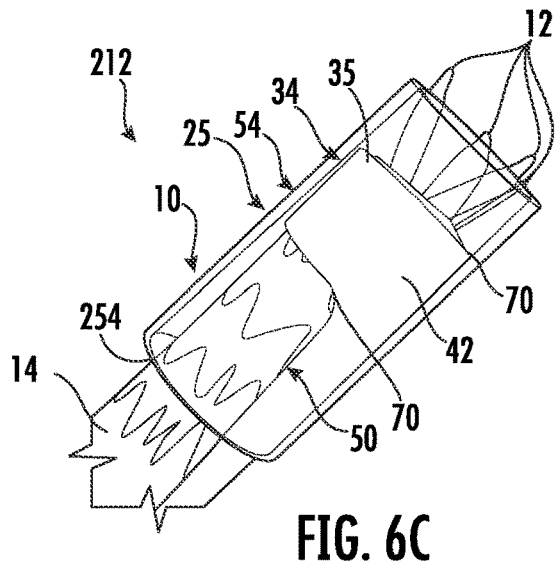
Figure 6D:
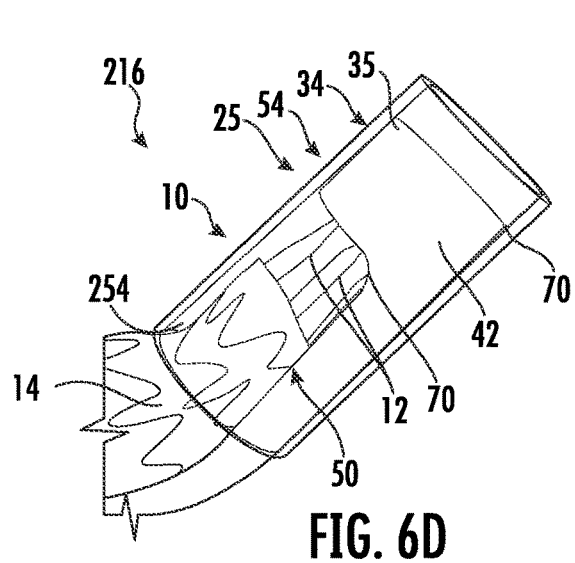
Figure 6E:
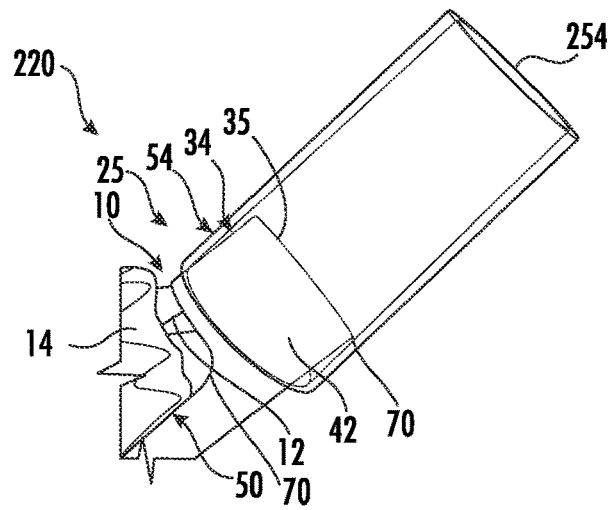

Referring now to FIGS. 5A-5B, a portion of the sidewall 42 of the first ring portion 54 (e.g., proximate the first aperture 35 and the opening 50) and the second ring portion 58 is shown cut-out of the endovascular stent graft extraction device 25. The sidewall 42 is shown to include a taper such that the sidewall 42 decreases in width from proximate the first aperture 35 to proximate the opening 50 (i.e., the hollow bore 43 is narrower proximate the first aperture 35 than proximate the opening 50). In some embodiments, the sidewall 42 of the first ring portion 54 includes a taper such that the width of the sidewall proximate the first aperture 35 is approximately 3-5 mm or approximately 4 mm and the width of the sidewall proximate the opening 50 is approximately 2-3 mm or approximately 2.8 mm. In some embodiments the sidewall of the second ring portion 58 also includes a taper such that the sidewall 42 decreases in width from proximate the second aperture 39 to proximate the opening 50. In some embodiments, the sidewall 42 of the second ring portion 58 includes a taper such that the width of the sidewall proximate the second aperture 39 is approximately 3-5 mm or approximately 4 mm and the width of the sidewall proximate the opening 50 is approximately 2-3 mm or approximately 2.8 mm. By increasing the diameter of the hollow bore 43 from the first aperture 35 and the second aperture 39 to the opening 50, the first ring portion 54 and the second ring portion 58 better receive the frame 14 and the prongs 12 of the endovascular stent graft 10. For example because the hollow bore 43 increases in diameter as the frame 14 is received by the first ring portion 54 or the second ring portion 58, the frame 14 contacts the sidewall 42 less and has less drag or friction with the sidewall 42. This allows the endovascular stent graft 10 to more easily slide (due to less friction or reduced drag) into the first ring portion 54 or the second ring portion 58 and better prevents unexpected movement of the endovascular stent graft 10. In some embodiments, while the sidewall 42 decreases in width from the first aperture 35 and the second aperture 39 to the opening 50, the outside diameter of the sidewall 42 stays the same and the inner diameter of the sidewall 42 decreases or tapers (i.e., the hollow bore 43 is narrower proximate the second aperture 39 and the first aperture 35 than proximate the opening 50). As a result, the portion of the sidewall 42 in contact with the walls of the aorta does not change in diameter, but the portion of the sidewall 42 in contact with the stent graft 10 decreases in diameter Additionally, the end of the sidewall 42 at the first open end 34 and directly proximate the opening 50 includes a blunt (e.g., smooth, rounded, etc.) edge 70. In use, the blunt edge 70 is the first thing to come into contact with the endovascular stent graft 10 implanted in the vessel. As a result, it is important that the blunt edge 70 is blunt or rounded to prevent a sharp contrast that may catch or become entangled with the frame 14, the vessel wall, and/or the prongs 12. In some embodiments, the blunt edge 70 includes a radius of curvature of approximately 1-3/mm or approximately 2/mm. By doing so, the blunt edge 70 naturally comes into contact with the prongs 12 and moves them from the deployed position to the non-deployed position without catching or becoming entangled with the prongs 12. Similarly, the sidewall 42 directly proximate the opening 50 may further include a second blunt edge 70 (for similar reasons as the first blunt edge 70). In this way, the prongs 12 do not catch on the sidewall 42 as they are leaving the opening 50 which could pull on the entire endovascular stent graft extraction device 25. Similar to the sidewall 42 at the first open end 34, the sidewall 42 at the second open end 38 also includes a blunt or rounded edge 70 (which may be similar to the blunt edge 70 at the first open end 34).

Referring now to FIGS. 6A-6E a method 200 of extracting an endovascular stent graft (e.g., the stent graft 10) from a vessel 254 (e.g., one or more sections of the aorta, one or more arteries, etc.) is shown, according to an exemplary embodiment. The method 200 commences at step 204 in which a clamp (e.g., a forceps) is used to grasp a portion of the endovascular stent graft 10. The clamp is used to grasp a portion (e.g., one or more portions of the frame 14) of the endovascular stent graft 10 so as to hold the endovascular stent graft 10 in place during movement of the extraction device 25 over the endovascular stent graft 10, and to later (after the prongs 12 are moved to the non-deployed state) pull out the endovascular stent graft 10. In some embodiments, prior to step 604, the vessel 254 itself is secured or clamped to prevent movement of the vessel 254 during the method 200. In other embodiments, multiple clamps may be used to grasp a portion of the endovascular stent graft 10. In further embodiments, a clamp may be used to grasp the endovascular stent graft extraction device 25 (e.g., by the sidewall 42).

Once the endovascular stent graft 10 is grasped by the clamp 258, the method 200 proceeds to step 208 in which an extraction device (e.g., the endovascular stent graft extraction device 25) is inserted into the vessel 254. The endovascular stent graft extraction device 25 may be inserted into the vessel 254 through one or more incisions in the vessel 254 and may be configured (e.g., the dimensions may be changed prior to 3D printing the endovascular stent graft extraction device 25) to fit inside of the vessel 254. In other embodiments and prior to use, the user of the endovascular stent graft extraction device 25 may determine the diameter of the vessel 254 and then determine which end of the endovascular stent graft extraction device 25 to insert into the vessel 254. As discussed herein, the first open end 34 and the second open end 38 include different outer (and inner) diameters, and the user may determine which is appropriate to be used on the vessel 254. In one embodiment, the vessel 254 may be approximately 26 mm in diameter and therefore the user may choose to insert the first open end 34 into the vessel 254 (as compared to the second open end 38).

Once the endovascular stent graft extraction device 25 has been inserted into the vessel 254, the method 200 proceeds to step 212 in which the endovascular stent graft extraction device 25 is slid over the stent graft 10 such that the first open end 34 slides over the stent graft 10 and that the sidewall 42 is located between the stent graft 10 and a wall of the vessel 254 to compress the stent graft 10 within the first ring portion 54. Once the first open end 34 comes into contact with the frame 14 of the stent graft 10, the blunt edge 70 and the taper of the sidewall 42 allow the frame 14 to easily slide (e.g., with little to no resistance) into the hollow cavity 43. It is therefore of use that the first aperture 35 has an inner diameter large enough to receive the stent graft 10. In some embodiments (in which the second open end 38 was inserted first into the vessel 254) the endovascular stent graft extraction device 25 is slid over the stent graft 10 such that the second open end 38 slides over the stent graft 10 and such that the sidewall 42 is located between the stent graft 10 and the wall of the vessel 254 to compress the stent graft 10 within the second ring portion 58.

After the endovascular stent graft extraction device 25 has been slid so the sidewall 42 is located between the stent graft 10 and the wall of the vessel 254, the method 200 proceeds to step 216 in which the endovascular stent graft extraction device 25 is further slid over the stent graft 10 until the endovascular stent graft extraction device 25 (e.g., blunt edge 70 of the sidewall 42) causes a prong (e.g., the prongs 12) to release (e.g., move from the deployed position to the non-deployed position) from the wall of the vessel 254. To do so, the blunt edge 70 of the sidewall 42 may push the prongs 12 radially inward and into the hollow bore 43 such that the sidewall 42 is between the prongs 12 and the wall of the vessel 254. In order to atraumatically remove the prongs 12, it is important that the prongs 12 do not catch on the sidewall 42 and therefore the sidewall 42 includes the blunt edge 70 and also tapers from the first aperture 35 and the second aperture 39 to the opening 50. In other embodiments, other components of the endovascular stent graft extraction device 25 may be configured to remove the prongs 212 from the wall of the vessel 254.

Once the prongs 12 are released from the wall of the vessel 254, the method 200 proceeds to step 220 in which the stent graft 10 and the endovascular stent graft extraction device 25 are fully removed from the vessel 254, concurrently or in sequence, with the sidewall 42 of the endovascular stent graft extraction device 25 located at least partially between the stent graft 10 and the vessel 254. At step 220, the clamp may be used to grasp at least one of the stent graft 10 and/or the endovascular stent graft extraction device 25 for removal (e.g., the clamp is used to extract or pull out either one). In some embodiments and at step 220, the stent graft 10 and the stent graft extraction device 25 are removed together, with the stent graft extraction device 25 continuing to push the prongs 212 radially inward to keep the prongs 25 from engaging the vessel 254. In this position, both the stent graft 10 and the stent graft extraction device 25 are removed from the vessel 254. In such embodiments, the stent graft 10 may be extracted from within the hollow bore 43 through the opening 50 after removal. In other embodiments, the stent graft 10 may be removed first, such that it is extracted from (e.g., is at least partially located within) the hollow bore 43 and through the opening 50. The stent graft 10 and the endovascular stent graft extraction device 25 are removed atraumatically from the vessel 254 such that they cause little to no damage to the vessel 254 itself. Because the sidewall 42 is located between the stent graft 10 and the vessel 254 as both are removed from the vessel 254, the vessel 254 does not (or minimally) comes into contact with the stent graft 10 and is better protected from damage. As compared to the stent graft 10 which includes the prongs 12, the sidewall 42 of the endovascular stent graft extraction device 25 is relatively smooth and therefore does not pull on or attach to the walls of the vessel 254.

Figure 7:
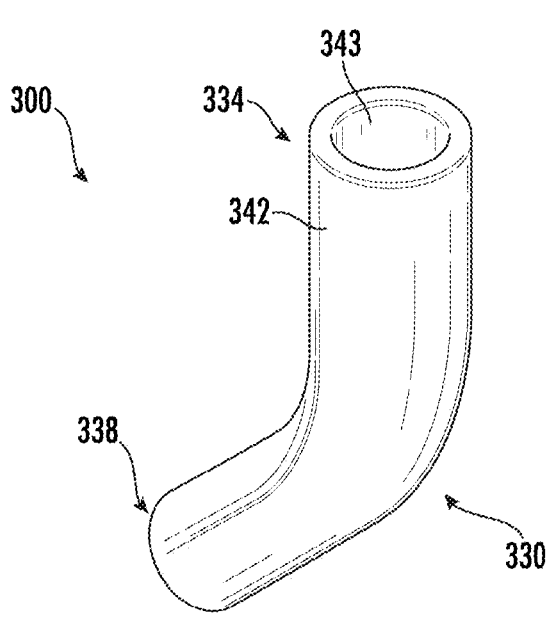
FIG. 7 is a perspective view of a second endovascular stent graft extraction device, according to another embodiment.

Referring now to FIG. 7, an endovascular stent graft extraction device 300 is shown according to an alternative embodiment. The endovascular stent graft extraction device 300 may be similar to the endovascular stent graft extraction device 25 and therefore similar reference numbers may be used for similar components. For example, the endovascular stent graft extraction device 300 includes a cylindrical body 330 that extends from a first open end 334 to a second open end 338. As compared to the endovascular stent graft extraction device 25, the device 300 is shown to not include the opening 50 such that the user can only access a hollow bore 343 defined by a sidewall 342 from the first open end 334 or the second open end 338. While doing so may prevent the user of the endovascular stent graft extraction device 300 from easily accessing the hollow bore 343, not including the opening 50 may provide for improved strength and rigidity of the sidewall 342.

Figure 8:
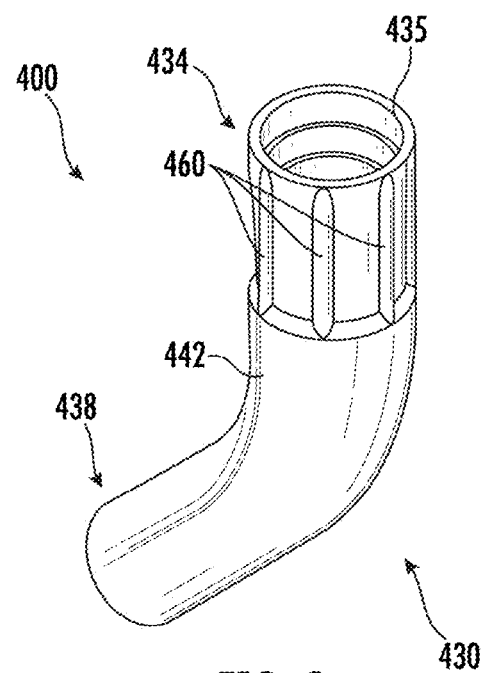
FIG. 8 is a perspective view of a third endovascular stent graft extraction device, according to another embodiment.

Referring now to FIG. 8, an endovascular stent graft extraction device 400 is shown according to an alternative embodiment. The endovascular stent graft extraction device 400 may be similar to the endovascular stent graft extraction device 25 and therefore similar reference numbers may be used for similar components. For example the endovascular stent graft extraction device 400 includes a cylindrical body 430 that extends from a first open end 434 to a second open end 438. As compared to the endovascular stent graft extraction device 25, the device 400 is shown to not include the opening 50, further includes one or more grips 460, and does not include the blunt edge 70. The grips 460 extend radially from the sidewall 442 (e.g., as a part of the sidewall 442) and along part of the length (e.g., from proximate the first aperture 435 to proximate a mid-portion) of the cylindrical body 430. In some embodiments, the grips 460 are configured to contact with the walls of the vessel 254 (e.g., the aorta, arteries, etc.) to better engage with and be received by the vessel 254. In some embodiments, the grips 460 better allow the endovascular stent graft extraction device 400 to slide along the walls of the vessel 254. In further embodiments, the grips 460 better allow the endovascular stent graft extraction device 400 to be grasped by the user (with or without a clamp) during the procedure.

Figure 9:
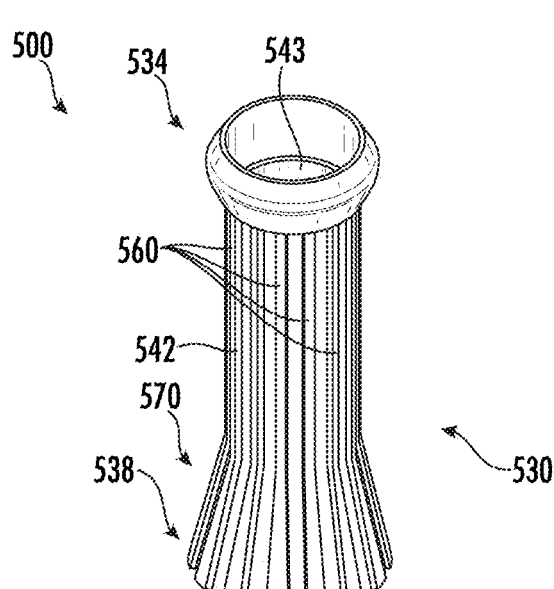
FIG. 9 is a perspective view of a fourth endovascular stent graft extraction device, according to another embodiment.

Referring now to FIG. 9, an endovascular stent graft extraction device 500 is shown according to an alternative embodiment. The endovascular stent graft extraction device 500 may be similar to the endovascular stent graft extraction device 25 and therefore similar reference numbers may be used for similar components. For example the endovascular stent graft extraction device 500 includes a cylindrical body 530 that extends from a first open end 534 to a second open end 538. As compared to the endovascular stent graft extraction device 25, the device 500 includes the cylindrical body 530 which is relatively straight (not curved), does not include the opening 50, further includes one or more grips 560, and does not include the blunt edge 70. The grips 560 (which may be similar to the grips 460) extend radially from the sidewall 542 (e.g., as a part of the sidewall 542) and along the entire length of the cylindrical body 530. Additionally, the device 500 has a bellowed portion 570 (e.g., an increase in outer diameter) from the proximate center of the device 500 to the second open end 538. In one embodiment, the bellow portion 570 extends approximately 30 mm from the second open end 538 towards the first open end 534 (i.e., the bellowed portion 570 is 30 mm in length). The bellowed portion 570 may be configured to contact and expand the walls of the vessel 254. In this way, the bellowed portion 570 may separate the frame 14 of the stent graft 10 from the walls of the vessel 254 and then better receive the frame 14 of the stent graft 10 within the hollow bore 543. In some embodiments, the bellowed portion 570 may have an outer diameter of approximately 36-40 mm or approximately 38 mm at the open end 538 and an outer diameter of approximately 28-32 mm or approximately 33 mm at the small end of the bellow portion 570.

Figure 10:
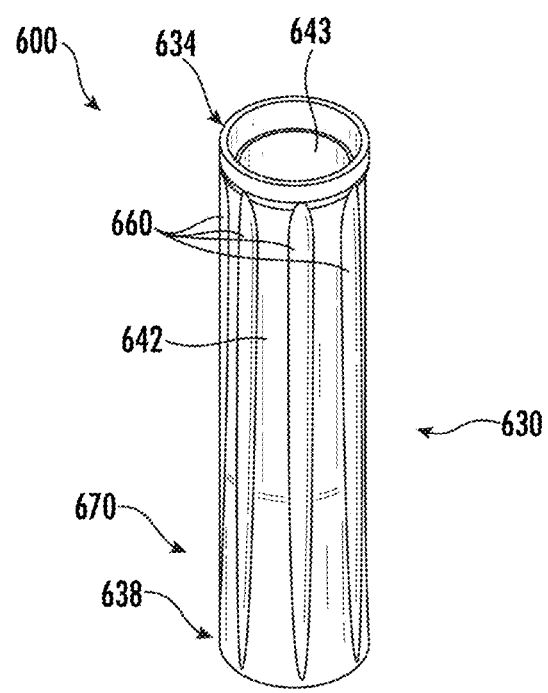
FIG. 10 is a perspective view of a fifth endovascular stent graft extraction device, according to another embodiment.

Referring now to FIG. 10, an endovascular stent graft extraction device 600 is shown according to an alternative embodiment. The endovascular stent graft extraction device 600 may be similar to the endovascular stent graft extraction device 25 and therefore similar reference numbers may be used for similar components. For example the endovascular stent graft extraction device 600 includes a cylindrical body 630 that extends from a first open end 634 to a second open end 638. As compared to the endovascular stent graft extraction device 25, the device 600 includes the cylindrical body 630 which is relatively straight (not curved), does not include the opening 50, further includes one or more grips 660, and does not include the blunt edge 70. The grips 660 (which may be similar to the grips 460) extend radially from the sidewall 642 (e.g., as a part of the sidewall 642) and along the entire (or most of the) length of the cylindrical body 630. Additionally, the device 600 has a bellowed portion 670 (e.g., an increase in outer diameter) from the proximate center of the device 600 to the second open end 638. The bellowed portion 670 is less prominent than the bellowed portion 570, but may still be configured to contact and expand the walls of the vessel 254. As a result, the bellowed portion 670 may have an outer diameter of approximately 21 mm at the open end 538 and an outer diameter of approximately 20 mm at the small end of the bellow portion 570. In this way, the bellowed portion 670 may separate the frame 14 of the stent graft 10 from the walls of the vessel 254 and then better receive the frame 14 of the stent graft 10 within the hollow bore 643.

Notwithstanding the embodiments described above with respect to the figures, various modifications and inclusions to those embodiments are contemplated and considered within the scope of the present disclosure.

It is also to be understood that the construction and arrangement of the elements of the systems and methods as shown in the representative embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed.

Accordingly, all such modifications are intended to be included within the scope of the present disclosure. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other illustrative embodiments without departing from scope of the present disclosure or from the scope of the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Similarly, unless otherwise specified, the phrase "based on" should not be construed in a limiting manner and thus should be understood as "based at least in part on." Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances, where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent Moreover, although the figures show a specific order of method operations, the order of the operations may differ from what is depicted. Also, two or more operations may be performed concurrently or with partial concurrence. All such variations are within the scope of the disclosure.

What is claimed is:

1. A device for extracting an endovascular stent graft from a vessel, comprising:
    a ring having a first open end and a second open end; and
    a sidewall extending away from the ring at the second open end;
    wherein:
        the sidewall is curved along a length of the device;
        the sidewall extends partially around a circumference of the second open end of the ring, such that the sidewall defines an open portion;
        a thickness of the ring at the first open end is greater than the thickness at the second open end; and
        the ring and the sidewall are rigid.

2. The device of claim 1, wherein a diameter of the first open end is in a range of 24 to 26 millimeters and a diameter of the second open end is in a range of 18 to 20 millimeters.

3. The device of claim 2, wherein the diameter of the first open end is approximately 25 millimeters and the diameter of the second open end is approximately 19 millimeters.

4. The device of claim 1, wherein a diameter of the first open end is at least 30 millimeters and a diameter of the second open end is approximately 27 millimeters.

5. The device of claim 1, wherein the length of the sidewall is approximately 100-150 millimeters.

6. The device of claim 1, wherein an edge of at least one of the first open end and the second open end of the ring is rounded to provide a smooth edge.

7. The device of claim 6, wherein the edge of the first open end of the ring is rounded and has a radius of curvature of approximately 1-3 mm.

8. The device of claim 1, wherein the ring and the sidewall are formed of a medical grade plastic or stainless steel.

9. A method of extracting an endovascular stent graft from a vessel, comprising:
    inserting an extraction device into the vessel, the extraction device comprising:
        a ring having a first open end and a second open end, and
        a sidewall extending away from the second open end;
        wherein:
            the sidewall is curved along a length of the extraction device;
            the sidewall extends partially around a circumference of the second open end of the ring, such that the sidewall defines an open portion;
            a thickness of the ring at the first open end is greater than the thickness at the second open end; and
            the ring and the sidewall are rigid;
    sliding the extraction device over the stent graft such that the sidewall slides between a vessel wall and the stent graft to compress the stent graft within the ring;

continue sliding the extraction device over the stent graft until the extraction device causes a prong of the stent graft to release from the vessel wall; and atraumatically removing at least one of the stent graft and the extraction device from the vessel while the sidewall of the extraction device is located at least partially between the stent graft and the vessel wall.

10. The method of claim 9, wherein removing at least one of the stent graft and the extraction device comprises sliding the stent graft and the extraction device concurrently from the vessel while the ring is positioned over the prong of the stent graft to push the prong radially inward thereby releasing the prong from the vessel wall.

11. The method of claim 9, further comprising 3-D printing the extraction device according to preferred specifications for a specific patient.

12. The method of claim 9, further comprising sterilizing the extraction device prior to first use or a subsequent use.

13. The method of claim 9, wherein a diameter of the first open end is in a range of 24 to 26 millimeters and a diameter of the second open end is in a range of 18 to 20 millimeters.

14. The method of claim 13, wherein the diameter of the first open end is approximately 25 millimeters and the diameter of the second open end is approximately 19 millimeters.

15. The method of claim 9, wherein a diameter of the first open end is at least 30 millimeters and a diameter of the second open end is approximately 27 millimeters.

16. The method of claim 9, wherein an edge of at least one of the first open end and the second open end of the ring is rounded to provide a smooth edge for sliding between the vessel wall and the stent graft.

17. The method of claim 16, wherein the rounded edge of the ring at the first open end has a radius of curvature of approximately 1-3 mm.

18. A device for extracting an endovascular stent graft from a vessel, comprising:
    a ring having a first open end and a second open end; and
    a sidewall extending away from the ring at the second open end;
    wherein:
        the sidewall is curved along a length of the device such that the sidewall intersects a central axis of the ring;
        a thickness of the ring at the first open end is greater than the thickness at the second open end; and
        the ring and the sidewall are rigid.

19. The device of claim 18, wherein the sidewall extends partially around a circumference of the second open end of the ring, such that the sidewall defines an open portion.

* * * * *